US006494882B1

(12) United States Patent
Lebouitz et al.

(10) Patent No.: US 6,494,882 B1
(45) Date of Patent: Dec. 17, 2002

(54) CUTTING INSTRUMENT HAVING INTEGRATED SENSORS

(75) Inventors: Kyle S. Lebouitz, Pittsburgh, PA (US); Michele Migliuolo, McMurray, PA (US)

(73) Assignee: Verimetra, Inc., Pittsburgh, PA (US)

( * ) Notice: Subject to any disclaimer, the term of this patent is extended or adjusted under 35 U.S.C. 154(b) by 16 days.

(21) Appl. No.: 09/626,273

(22) Filed: Jul. 25, 2000

(51) Int. Cl.[7] ............................................... A61B 18/18
(52) U.S. Cl. ....................................................... 606/45
(58) Field of Search ........................... 606/1, 166, 167, 606/32, 34, 35, 29, 45, 172, 181, 190; 600/547, 554, 564, 587, 555; 30/342, 346.5; 83/72–74, 76.7, 364, 522.11, 522.14, 522.15, 522.21; 294/907; 340/407.1, 407.2

(56) References Cited

U.S. PATENT DOCUMENTS

| | | | |
|---|---|---|---|
| 4,089,336 A | 5/1978 | Cage et al. | |
| 4,091,813 A | 5/1978 | Shaw et al. | |
| RE30,190 E | 1/1980 | Shaw | |
| 4,219,025 A | 8/1980 | Johnson | |
| 4,364,390 A | 12/1982 | Shaw | |
| RE31,723 E | 11/1984 | Shaw | |
| 4,515,168 A | 5/1985 | Chester et al. | |
| 4,534,827 A | 8/1985 | Henderson | |
| 4,540,002 A | 9/1985 | Atlas | |
| 4,674,498 A | 6/1987 | Stasz | |
| 4,697,489 A | 10/1987 | Kim | |
| 4,798,000 A | 1/1989 | Bedner et al. | |
| 4,802,476 A | * 2/1989 | Noerenberg et al. | 128/303.14 |
| 4,850,353 A | 7/1989 | Stasz et al. | |
| 4,860,744 A | 8/1989 | Johnson et al. | |
| 4,922,903 A | 5/1990 | Welch et al. | |
| 4,936,281 A | 6/1990 | Stasz | |
| 4,960,419 A | 10/1990 | Rosenberg | |

(List continued on next page.)

FOREIGN PATENT DOCUMENTS

| | | |
|---|---|---|
| DE | 43 21 254 | 1/1995 |
| EP | 0 294 063 | 12/1988 |
| EP | 0 349 443 | 1/1990 |

OTHER PUBLICATIONS

"Thin Film Process," V–1, Chemical Etching, pp. 401–496, W. Kern & C. Deckert, Academic Press, Inc., 1998.

(List continued on next page.)

Primary Examiner—Jeffrey R. Jastrzab
Assistant Examiner—Frances P. Oropeza
(74) Attorney, Agent, or Firm—Finnegan, Henderson, Farabow, Garrett & Dunner, L.L.P.

(57) ABSTRACT

A cutting instrument including a metal blade has a recess formed therein and a semiconductor substrate affixed to the blade in the recess. The semiconductor substrate includes at least one sensor formed thereon. The sensor formed on the semiconductor substrate may comprise at least one or an array of a strain sensors, pressure sensors, nerve sensors, temperature sensors, density sensors, accelerometers, and gyroscopes. The cutting instrument may also further include a handle wherein the blade is affixed to the handle and the semiconductor substrate is electrically coupled to the handle. The handle may then be coupled, either physically or by wireless transmission, to a computer that is adapted to display information to a person using the cutting instrument based on signals generated by one or more of the sensors formed on the semiconductor substrate. The computer or handle may also be adapted to store data based on the signals generated by one or more of the sensors. A method of making said cutting instrument includes the steps of at least one sensor being formed on a semiconductor wafer and a layer of photoresist being applied on a top side of the semiconductor wafer according to a pattern that matches the defined shape of the semiconductor substrate. The portion of the semiconductor wafer not covered by the photoresist is removed and thereafter the photoresist is removed from the semiconductor wafer, thereby leaving the semiconductor substrate having a defined shape and at least one sensor formed thereon. The semiconductor substrate having a defined shape and at least one sensor formed thereon is then affixed to a metal blade in a recess formed in the blade.

56 Claims, 11 Drawing Sheets

U.S. PATENT DOCUMENTS

| | | | |
|---|---|---|---|
| 4,962,766 A | | 10/1990 | Herzon |
| 4,980,021 A | | 12/1990 | Kitamura et al. |
| 4,980,646 A | | 12/1990 | Zemel |
| 5,026,387 A | | 6/1991 | Thomas |
| 5,129,262 A | | 7/1992 | White et al. |
| 5,189,914 A | | 3/1993 | White et al. |
| 5,306,287 A | | 4/1994 | Becker |
| 5,317,938 A | | 6/1994 | deJuan, Jr. et al. |
| 5,467,656 A | * | 11/1995 | Teare et al. |
| 5,579,583 A | * | 12/1996 | Mehregany et al. .......... 30/342 |
| 5,609,607 A | | 3/1997 | Hechtenberg et al. |
| 5,645,564 A | | 7/1997 | Northrup et al. |
| 5,728,089 A | | 3/1998 | Lal et al. |
| 5,779,642 A | | 7/1998 | Nightengale |
| 5,792,137 A | | 8/1998 | Carr et al. |
| 5,797,898 A | | 8/1998 | Santini, Jr. et al. |
| 5,807,261 A | | 9/1998 | Benaron et al. |
| 5,842,387 A | | 12/1998 | Marcus et al. |
| 5,928,158 A | | 7/1999 | Aristides |
| 5,980,518 A | | 11/1999 | Carr et al. |
| 5,987,346 A | | 11/1999 | Benaron et al. |
| 6,009,623 A | * | 1/2000 | Orloff |

OTHER PUBLICATIONS

"The Etching of Silicon with XeF2 Vapor," H.F. Winters & J.W. Coburn, American Institute of Physics, Appl. Phys. Lett. 34(1), pp. 70–73, Jan. 1979.

"MOS Integrated Silicon Pressure Sensor," Tanigawa, et al., IEEE Trans. Electron Devices, vol. ED–32, No. 7, pp. 1191–1195, Jul. 1985.

"Micro–Diaphragm Pressure Sensor," Sugiyama, et al., IEEE Int. Electron Devices Meeting, 1986, pp. 184–187.

"A Multisensor Employing an Ultrasonic Lamb–Wave Oscillator," Wenzel, et al., IEEE Trans. Electron Devices, vol. 35, No. 6, pp. 735–743, Jun. 1988.

"A Low Cost Monolithic Accelerometer," Sherman, et al., Symposium on VLSI Circuits Digest of Technical Papers, pp. 34–35, 1992.

"Silicon Processed Microneedles," Lin, et al., 7th International Conference on Solid State Sensors and Actuators, Transducers, Jun. 1993, pp. 237–240.

"Microelectronic Circuits," A.S. Sedra and K.C. Smith, Terminal Characteristics of Junction Diodes, 4th Ed., p. 135, Oxford University Press, New York, 1998.

"Design and Fabrication of a High–Performance Polysilicon Vibrating Ring Gyroscope," Ayazi, et al., Proc. IEEE MEMS 98, pp. 621–626, 1998.

"Microneedles and Microlancets Fabricated Using SOI Wafers and Isotropic Etching," Lebouitz, et al., Electrochemical Society Proceedings, vol. 98–14, pp. 235–244.

* cited by examiner

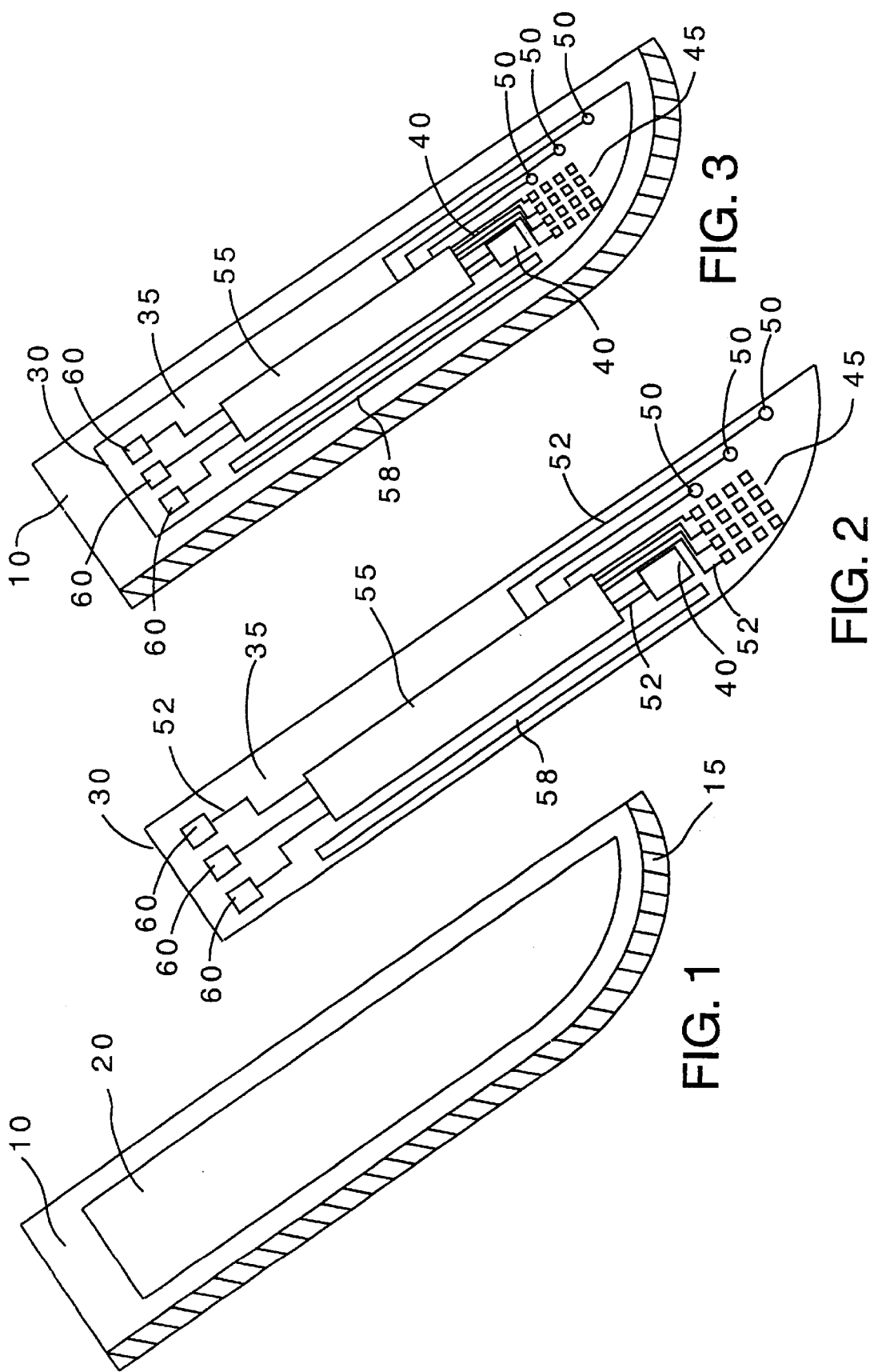

CUTTING INSTRUMENT HAVING INTEGRATED SENSORS

FIELD OF THE INVENTION

The present invention relates to a cutting instrument having a variety of sensors integrated therein. More particularly, the invention relates to a blade having a sensor or sensors formed thereon, wherein the sensors are mounted adjacent the cutting surface to allow measurement of the physical characteristics of the blade and a workpiece or tissue.

BACKGROUND OF THE INVENTION

Cutting instruments exist for a myriad of applications, ranging from very specialized applications such as surgical scalpels, to industrial applications and common consumer applications.

Surgery continues to be one of the most delicate and risky medical procedures. Before making an incision into tissue, surgeons are required to identify what type of tissue is being incised, such as fatty, muscular, vascular or nerve. This task is greatly complicated by the fact that human anatomy differs slightly from person to person. The failure to properly classify tissue before making an incision can have severe adverse consequences. For example, if a surgeon fails to properly classify a nerve and cuts it, then the patient can suffer effects ranging from a loss of feeling to loss of motor control.

Thus, it would be useful to surgeons to be able to sense during surgery, and more particularly during the actual cutting operation, certain characteristics that would help to identify and classify the substrate tissue. For example, by sensing the amount of force being applied with a blade, the resistance of the tissue can be measured and can be used to assist in the classification of the tissue. Sensing the different pressure characteristics of material surrounding a blade, for example in the surrounding fluid, can help to classify the type or types of tissue surrounding the blade or the regions of the body being cut by the blade. Sensing the density of the tissue in proximity with the blade can also be used to assist in the identification of that tissue. Finally, as noted above, sensing the presence of nerve tissue can prevent the inadvertent cutting thereof. Moreover, the ability to sense the type of tissue in proximity with or cut by a blade would not only be useful to provide real time feedback for surgeons during surgery, but would also be useful if recorded for later use for tracking purposes.

Temperature can also be used to monitor the usage of a blade. For example, by monitoring the time for which a blade is at approximately 98.6 degrees Fahrenheit, the length of time that the blade has been in use can be determined. Also, information relating to the extent and direction of movement of a blade can useful both while the blade is being used and afterward for monitoring purposes, such as to measure the amount of cutting done in a procedure.

The ability to sense one or more of the parameters just described would also be useful in non-medical/surgical applications. For example, in connection with a consumer blade such as a razor blade, measurement of one or more of these parameters may be used to give consumers information regarding the cutting force applied to the blade, the materials being cut, and to estimate the sharpness of the blade. Furthermore, the manufacturers that design consumer blades may use the measured parameters to assess the impact of cutting tool design changes. For example, a razor blade manufacturer could quantify the changes in applied force to a blade that are due to changes in the handle or blade configuration. Similarly, in connection with machining tools such as a saw blade and milling tools, measurement of one or more of these parameters can be used to determine or predict the sharpness and cutting performance of the tool.

Sensor technology that can be integrated into semiconductor materials for sensing characteristics such as strain, pressure, temperature, density, the presence of nerves and movement are well known in the art. A strain sensor or gauge can be constructed using a resistor made of a material such as polysilicon. The resistance of a material such as polysilicon changes as it is stretched, and by measuring the change in resistance, one can calculate the strain. A pressure sensor can be constructed by placing a strain sensor on top of a diaphragm made of a material such as silicon nitride or polysilicon. When the diaphragm moves due to surrounding pressure changes, the strain gauge can be used to measure the local pressure. Examples of such pressure sensors are described in S. Sugiyama et al., "Micro-diaphragm Pressure Sensor," IEEE Int. Electron Devices Meeting, 1986, pp. 184–7, and H. Tanigawa et al., "MOS Integrated Silicon Pressure Sensor," IEEE Trans. Electron Devices, Vol. ED-32, No. 7, pp. 1191–5, July 1985, the disclosures of which are incorporated herein by reference.

One example of a temperature sensor can be constructed in a manner similar to a strain sensor using a resistor made of a material such as polysilicon. Using this type of a sensor, temperature can be measured as a function of the change in the resistance of the material. Similarly, as described in A. S. Sedra and K. C. Smith, "Microelectronic Circuits," $4^{th}$ Ed., Oxford University Press, New York, p. 135, 1998, the disclosure of which is incorporated herein by reference, diodes have an easily measured temperature dependence and thus are also used in designing temperature sensors.

Piezoelectric ultrasonic sensors can be used to measure density. Such sensors vibrate at a high frequency and emit, in the direction of the object of interest, a high frequency signal. Density of the impinged object can then be measured based on the signal that is reflected back by that object. Examples of such sensors are described in White et al., U.S. Pat. No. 5,129,262, entitled "Plate-mode Ultrasonic Sensor," White et al., U.S. Pat. No. 5,189,914, also entitled "Plate-mode Ultrasonic Sensor," and S. W. Wenzel and R. M. White, "A Multisensor Employing an Ultrasonic Lamb-wave Oscillator," IEEE Trans. Electron Devices, Vol. 35, No. 6, pp. 735–743, June 1988, the disclosures of which are incorporated herein by reference. It is well known to sense the presence of nerve tissue using an electrical contact, such as a gold electrode, which picks up and conducts electrical signals in proximity therewith.

Movement or motion can be detected using an accelerometer, which measures acceleration. The signal output of an accelerometer can be integrated to determine or predict the distance traveled by a reference object. An example of an accelerometer integrated into semiconductor materials is described in Sherman, S. J.; Tsang, W. K.; Core, T. A.; Quinn, D. E., "A low cost monolithic accelerometer," 1992 Symposium on VLSI Circuits. Digest of Technical Papers, Seattle, Wash., USA, Jun. 4–6 1992, p. 34–5, the disclosure of which is incorporated herein by reference. This accelerometer operates by monitoring the deflection of a polysilicon structure, which can then be used to determine or predict acceleration, and is produced using the micromachining of layers of semiconductor materials using semiconductor processing techniques. Direction of movement or motion can be detected using a gyroscope. An example of a gyroscope that can be integrated into semiconductor materials described in Ayazi, F.; Najafi, K., "Design and fabrication of high-performance polysilicon vibrating ring gyroscope." Proc. IEEE MEMS 98, p. 621–6, 1998, the disclosure of which is incorporated herein by reference. This gyroscope operates by monitoring the movement of a vibrating ring of silicon to infer change in direction, and is produced using the micromachining of layers of semiconductor materials using semiconductor processing techniques.

Surgical tools constructed entirely of semiconductor materials, such as silicon, having the ability to sense, for example, temperature or strain, are known, examples of which are described in Carr et al., U.S. Pat. No. 5,980,518, entitled "Microcautery Surgical Tool," and Mehregany et al., U.S. Pat. No, 5,579,583, entitled "Microfabricated Blades." Using only semiconductor materials to construct the surgical tools is a natural approach since semiconductor materials such as silicon can be made with the requisite degree of sharpness and will also allow for direct fabrication of circuitry. However, semiconductor materials such as silicon tend to be brittle and hence not well suited for use as the primary structural component in a cutting device for surgical, industrial, and many consumer applications.

SUMMARY OF THE INVENTION

Described is a cutting instrument including a rigid blade having a recess formed therein and a semiconductor substrate affixed to the blade in the recess. The blade is preferably constructed of metal. The semiconductor substrate includes at least one sensor formed thereon. The sensor formed on the semiconductor substrate may comprise one or more of a strain sensor, a pressure sensor, a nerve sensor, a temperature sensor, a density sensor, an accelerometer, and a gyroscope. The sensor formed on the semiconductor substrate may also comprise an array of two or more of each sensor.

The recess in the blade is preferably formed so as to follow at least a portion of the edge of the blade. The semiconductor substrate may then be affixed to the blade in the recess adjacent the edge of the blade. The semiconductor substrate may also include circuitry formed thereon that is coupled to the sensors. The circuitry preferably includes one or more amplifiers and/or logic circuits for multiplexing the signals generated by the sensors.

The cutting instrument may also further include a handle wherein the blade is affixed to the handle and the semiconductor substrate is electrically coupled to the handle. The handle may then be coupled to a computer that is adapted to display information to a person using the cutting instrument based on signals generated by one or more of the sensors formed on the semiconductor substrate. The handle may include an electrical connector that is physically connected to a compatible connector associated with the computer, or may preferably include a wireless transmitter coupled the semiconductor substrate that is in communication with a wireless receiver associated with the computer. The handle or separate computer may also be adapted to store data based on the signals generated by one or more of the sensors.

Also described is a method of making a cutting instrument, including a semiconductor substrate having a defined shape and at least one sensor formed thereon. According to the method, at least one sensor is formed on a semiconductor wafer and a layer of photoresist is applied on a top side of the semiconductor wafer according to a pattern that matches the defined shape of the semiconductor substrate. The portion of the semiconductor wafer not covered by the photoresist is removed and thereafter the photoresist is removed from the semiconductor wafer, thereby leaving the semiconductor substrate having a defined shape and at least one sensor formed thereon utilizing techniques well known in the art. The semiconductor substrate having a defined shape and at least one sensor formed thereon is then affixed to a metal blade in a recess formed in said blade.

The semiconductor wafer may comprise a silicon-on-insulator wafer including a top layer of silicon, a middle layer of insulating material, and a bottom layer of silicon. The method would then include removing the bottom layer of silicon after applying the photoresist. An etching process may be used to remove the portion of the semiconductor wafer not covered by the photoresist and the bottom layer of silicon.

The semiconductor wafer may also comprise a silicon wafer. The method may then include grinding the wafer down to a desired thickness before affixing the semiconductor substrate to the blade.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which:

FIG. 1 is an isometric view of a blade having a recess according to an aspect of the present invention;

FIG. 2 is a top plan view of a sensor element according to an aspect of the present invention;

FIG. 3 is an isometric view of the blade of FIG. 1, having the sensor element of FIG. 2 mounted therein;

DESCRIPTION OF THE PREFERRED EMBODIMENTS

Figure 4:
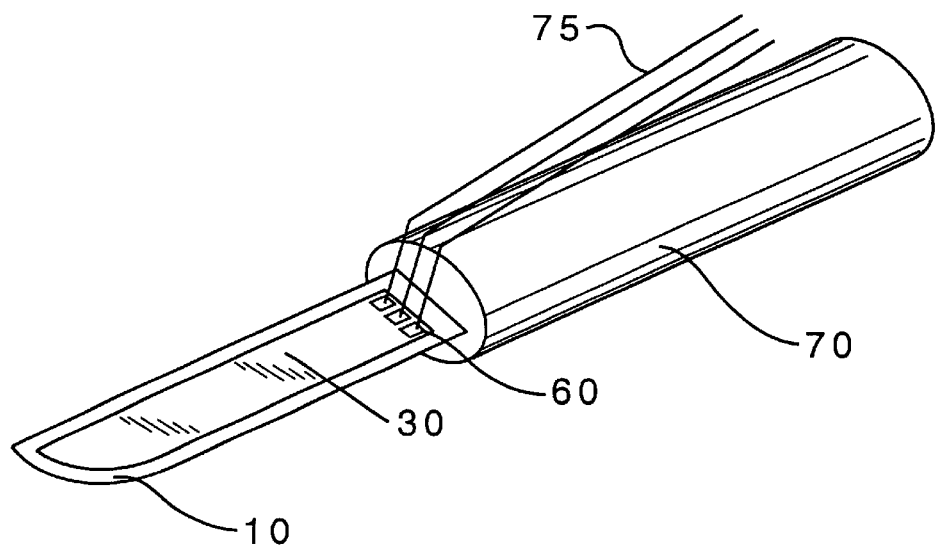
FIG. 4 is an isometric view of a blade according to the present invention affixed to a handle.

Referring to FIG. 1, blade 10, preferably made of a metal such as stainless steel, includes sharp edge 15 and recess 20 formed therein. As shown in FIG. 1, the shape of recess 20 preferably follows the shape of edge 15 of blade 10 so as to maximize the ability to increase the density of the sensors located at or near edge 15. Recess 20 can be formed in blade 10 by one of several well known methods including grinding, milling, chemical etching, water-jet machining, stamping, or electron discharge machining. Although only a single recess 20 is shown on a single side of blade 10 in FIG. 1, it should be understood that recess 20 may be formed on either one of the sides of blade 10, or both sides of blade 10. Additionally, multiple recesses of the same or different size and/or arrangement may be formed on one or both sides of blade 10.

Referring to FIG. 2, a sensor element 30 is shown. Sensor element 30 includes semiconductor substrate 35, preferably made of silicon. Formed on semiconductor substrate 35 are sensor 40 and sensor array 45, comprising a plurality of individual sensors. Sensor 40 and the individual sensors forming sensor array 45 can be any one of the well known types of sensors described herein, for example, a strain sensor, a pressure sensor, a temperature sensor, a density sensor, a motion sensor, or any other sensing device that can be formed on semiconductor substrate 35. Also formed on semiconductor substrate 35 are one or more electrodes 50, which are preferably gold electrodes. Other materials can be used to make electrodes 50, such as polysilicon, tungsten, platinum, titanium, aluminum, and palladium. As described above, electrodes 50 can be used to sense the presence of nerve or other types of tissue. Although one sensor 40, one sensor array 45, and three electrodes 50 are shown in FIG. 2, it will be apparent to one of skill in the art that any combination of one or more sensors 40, one or more sensor arrays 45, and/or one or more electrodes 50 may be formed on semiconductor substrate 35 without departing from the present invention. It is to be specifically understood that the elements, such as sensor 40, sensor array 45 and electrodes 50, may reside entirely on the surface of semiconductor substrate 35 and alternatively having least a portion, if not the entirety, of the element below the surface of semiconductor substrate 35 within the ambit of formation on the semiconductor substrate 35.

Sensor 40, sensor array 45 and electrodes 50 are coupled to circuitry 55 formed on semiconductor substrate 35 using electrical traces 52 made of a material such as aluminum, tungsten, or titanium. Circuitry 55 preferably comprises an amplifier coupled to each of sensor 40, sensor array 45 and electrodes 50. Circuitry 55 also preferably includes conventional logic circuitry coupled to the above described amplifiers for multiplexing the signals coming from sensor 40, sensor array 45 and electrodes 50 such that a single signal is output by circuitry 55 and ultimately by sensor element 30. Circuitry 55 could also be used as a mechanism to provide identification of the blade to the surgical system by having an embedded serial number. This serial number can then be used by the system to determine such parameters as the type of blade, the number of sensors, and the performance specifications of the sensors. Furthermore, the serial number could be compared to databases of used surgical tools to prevent the reuse, or in the case of non-disposable devices, prevent the overuse of the surgical tool. Circuitry 55 may be formed by well known CMOS or bi-polar device processing techniques. Circuitry 55 is coupled to electrical contacts 60, which include a positive contact, a negative contact, and a signal contact. Electrical contacts 60 provide the means for the multiplexed signal output by circuitry 55 to be output by sensor element 30.

In an alternative embodiment, rather than multiplexing the signals output by sensor 40, sensor array 45 and electrodes 50 so that the multiplexed signal can be output through a single electrical contact 60, each of the signals output by sensor 40, sensor array 45 and electrical contact 50 could be coupled to its own associated electrical contact 60 for outputting its signal from sensor element 30.

As shown in FIG. 2, semiconductor substrate 35 may include an enclosed fluid channel 58 for delivering a fluid to the cutting location of the blade, such as an anesthetic or medication. Alternatively, a lubricant or other fluid can be delivered in an industrial or consumer application. An example of a fabrication process that can be used to create fluid channel 58 is described in K. S. Lebouitz and A. P. Pisano, "Microneedles and Microlancets Fabricated Using SOI Wafers and Isotropic Etching," Proceedings of the Electrochemical Society, Vol 98–14, pp.235–244, 1998 and in L. Lin, A. P. Pisano, R. S. Muller, "Silicon Processed Microneedles," $7^{th}$ International Conference on Solid State Sensors and Actuators, Yokohama, Japan, Jun. 7–10, 1993, pp. 237–240, the disclosure of which is incorporated herein by reference. Fluid channel 58 may be pre-filled with the fluid, which is then allowed to seep out during the cutting operation, or, alternatively, fluid channel 48 may be connected to a source of fluid, such as a pump, using an external tube, not shown. Alternatively, a microchip drug delivery device such as those described in Santini et al., U.S. Pat. No. 5,797,898, the disclosure of which is incorporated herein by reference, may be included as part of semiconductor substrate 35. As an alternate application, fluid channel 58 may also be used to sample fluid from a patient or workpiece.

Referring to FIG. 3, sensor element 30, as described above, is bonded into recess 20 of blade 10 using any one of a number of adhesives, such as epoxy or cyanoacrylate glue, or by using eutectic bonding. As will be apparent to one of skill in the art, various alternative methods of bonding the sensor element 30 into the recess 20 of blade 10 are available, and any will be applicable so long as the bond is strong enough to prevent sensor element 30 from being dislodged from blade 10. Preferably, biocompatible materials are used in the bonding process.

Figure 5:
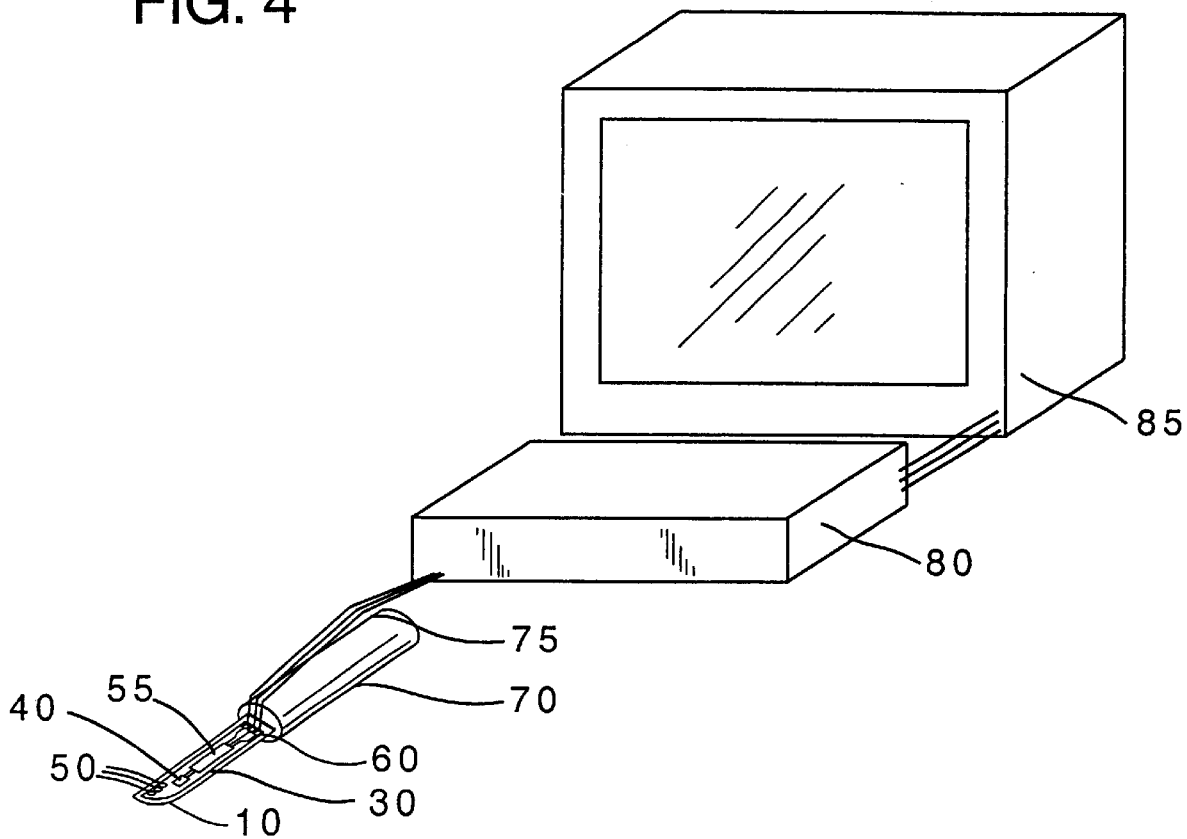
FIG. 5 is an isometric view of the blade and handle of FIG. 4 coupled to an interface and a computer.

Referring to FIGS. 4 and 5, according to an embodiment of the present invention, blade 10 with bonded sensor element 30 is mounted to handle 70 using any conventional mounting methods such as an adhesive or fasteners such as screws or clips. Wires 75 are attached to electrical contacts 60 by one of various well known wire bonding techniques. Wires 75 are in turn connected to interface unit 80. Interface unit 80 provides any necessary electrical power and may provide signal conditioning, such as filtering and amplification. Also, interface unit 80 may provide analog to digital conversion to convert the typically analog signals from sensor 40, sensor array 45, and electrodes 50 to computer usable digital signals. Interface 80, is in turn is coupled to computer 85, such as a conventional personal computer.

Computer 85 collects and analyzes the signals output by sensor element 30 and displays an output that will assist the surgeon using the cutting instrument. The analysis may include comparing the signals to a database of known tissue or workpiece parameters to identify the type of tissue or material being cut. Computer 85 may then display on the screen possible tissue or material types that match the analysis. Furthermore, Computer 85 may display the measured parameters such as temperature, force applied, density, and pressure. Computer 85 may also provide direct tactile, visual, or audible feedback to the surgeon or operator. For example, a surgeon can select a mode whereby the level of force applied to blade 10 is converted into a sound which, for example, could change in pitch with applied force. Also, computer 85 may store the collected signals for later use.

Figure 6:
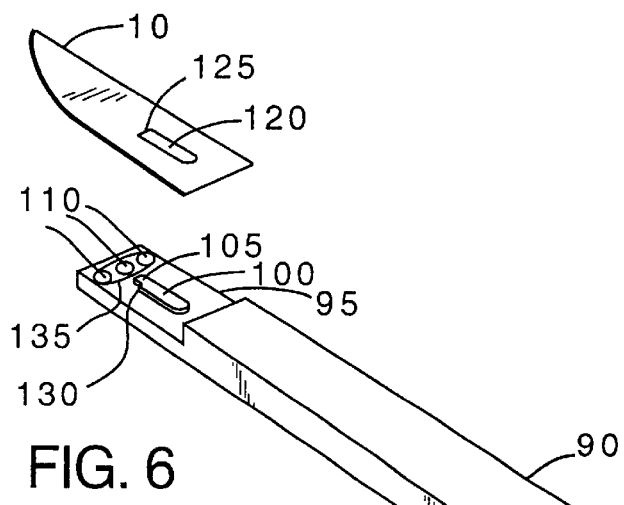
FIGS. 6 and 7 are top and bottom isometric views, respectively, of a blade and handle according to an alternate embodiment of the present invention that include a structure for connecting and electrically coupling the blade to the handle.
Figure 7:
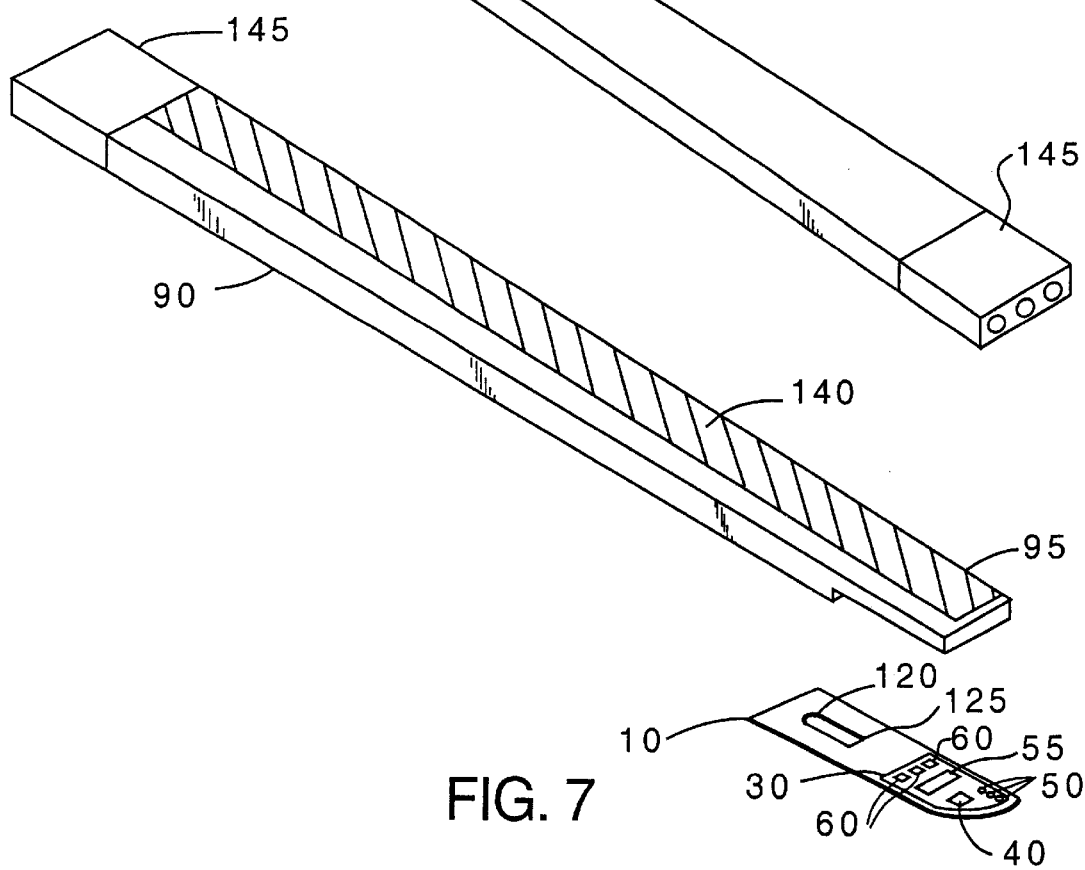
Figure 8:
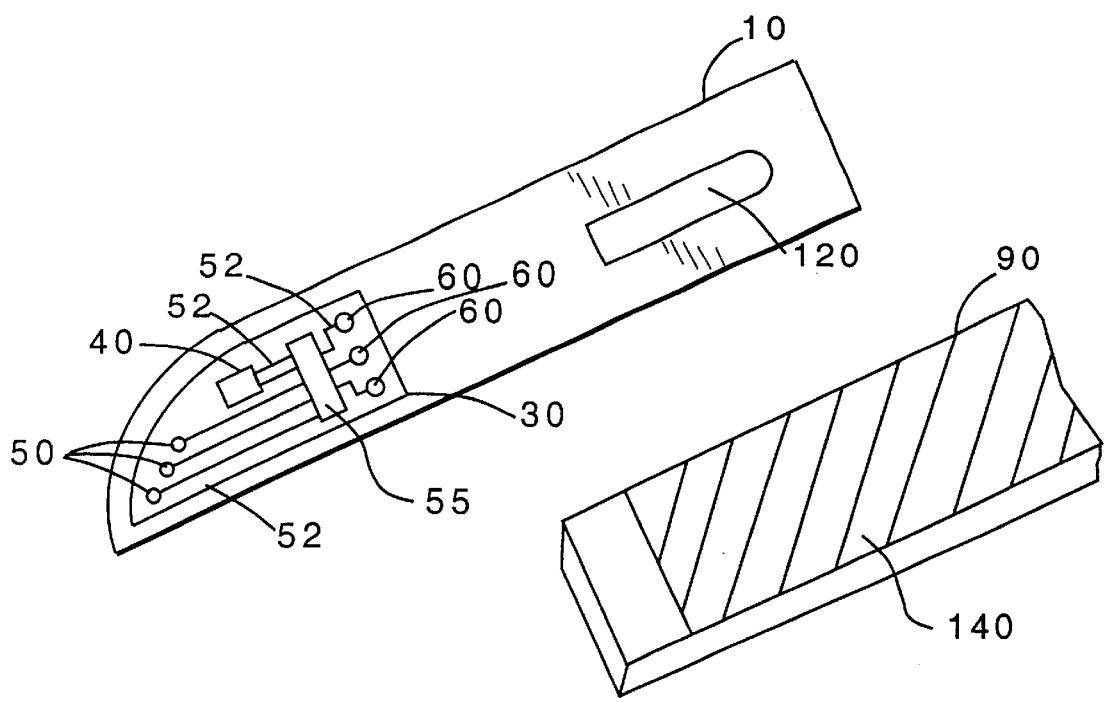
FIGS. 8 and 9 are more detailed isometric views of a portion of FIGS. 7 and 6, respectively.
Figure 9:
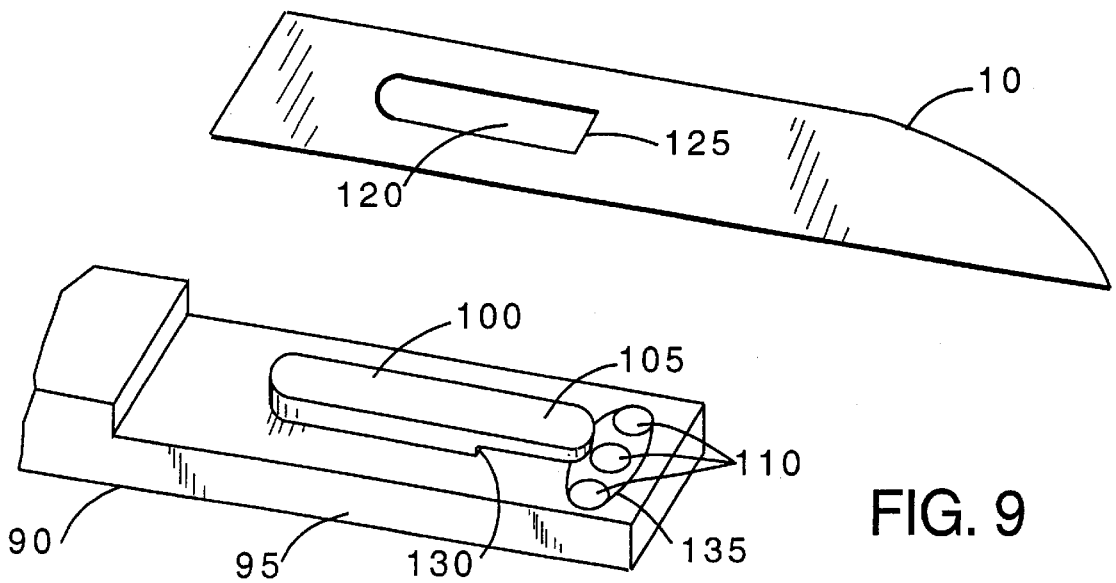
Figure 10:
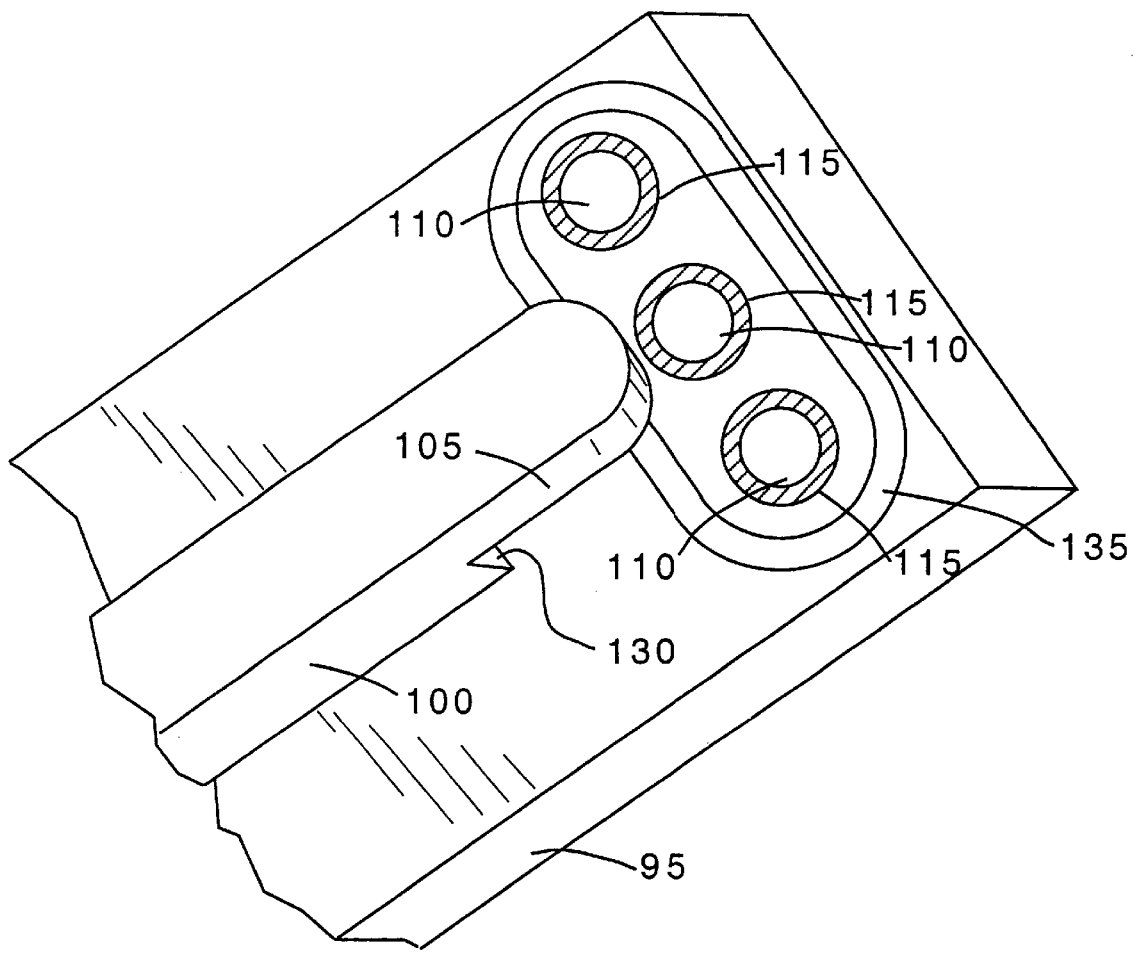
FIG. 10 is a more detailed isometric view showing a portion of the handle of FIGS. 6 through 9, and specifically a portion of the connecting and coupling structure of FIGS. 6 through 9.

FIGS. 6 through 10 show an alternative embodiment of the present invention having an alternative structure for connecting and electrically coupling blade 10 having sensor element 30 affixed thereto to handle 90. As can be seen in FIGS. 6, 9 and 10, handle 90 has located at a blade end 95 thereof fastener 100 having flange 105. Also located at blade end 95 of handle 90 are connectors or contacts 110 that penetrate the thickness of handle 90 and are surrounded by an electrical insulator 115 such as ceramic or plastic. Connectors 110 preferably comprise short metal wires, and most preferably comprise short gold wires.

According to this embodiment, blade 10 includes cutout 120 shown in FIGS. 6 through 9. Cutout 120 is through the entire thickness of blade 10, thus creating a hole in blade 10, and is at least as large as fastener 110. Blade 10 is affixed to handle 90 by first inserting fastener 110 of handle 90 through cutout 120 of blade 10, and then sliding blade 10 toward the end of handle 90 opposite blade end 95 so that flange 105 extends over a solid portion of blade 10 adjacent cutout 120 and so that end portion 125 of cutout 120 abuts wall 130 of fastener 100 located below flange 105. As will be apparent, it is necessary to perform this operation with the side of blade 10 having sensor element 30 bonded thereto facing the fastener 100. By doing so, the connectors 110 will mate with electrical contacts 60 of sensor element 30. A seal between handle 90 and blade 10 is provided by O-ring 135 shown in FIGS. 6, 9 and 10. As seen in FIGS. 7 and 8, handle 90 includes ribbon connector 140 located on a side opposite fastener 100. Ribbon connector 140 is electrically coupled to connectors 110, and leads to an electrical connector 145 located at the end of handle 90 opposite blade end 95. Electrical connector 145 can be utilized to couple handle 90 having blade 10 affixed thereto to an interface and/or computer such as those described above.

Figure 11A:
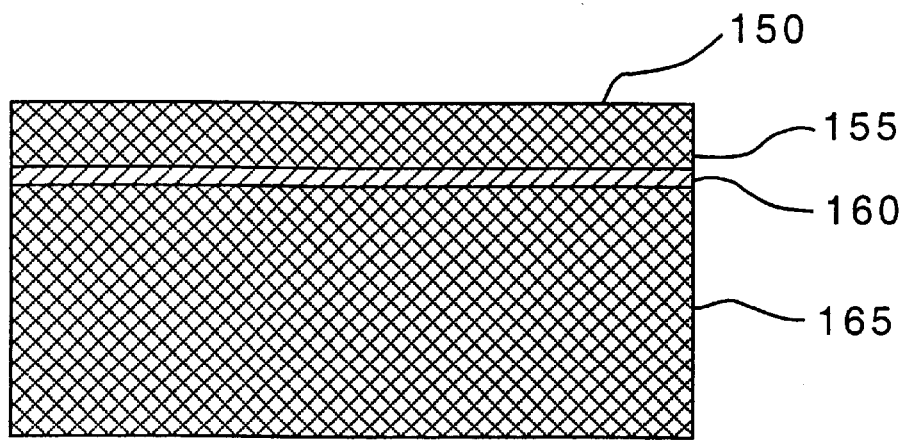
FIGS. 11a through 11e are cross-sectional views illustrating the steps of a method of making the sensor element of FIG. 2.
Figure 11B:
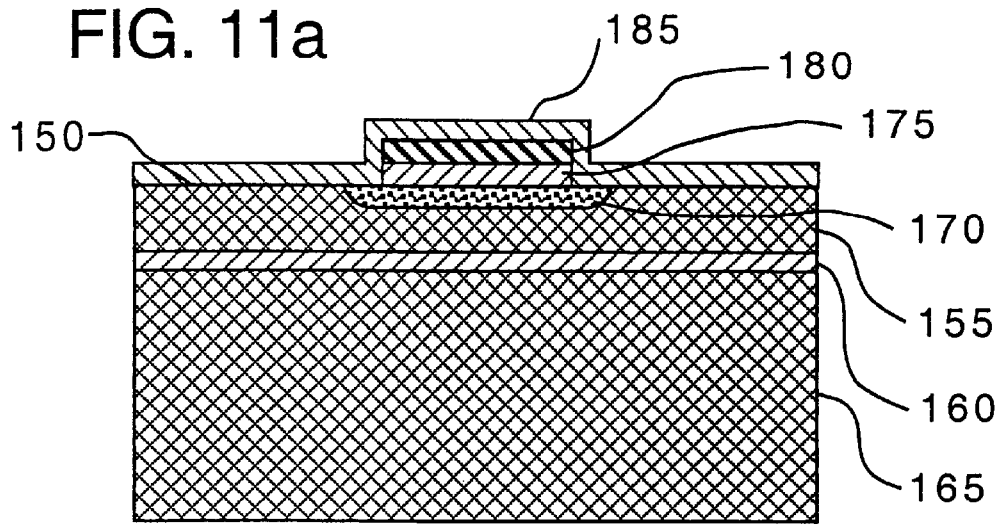
Figure 11C:
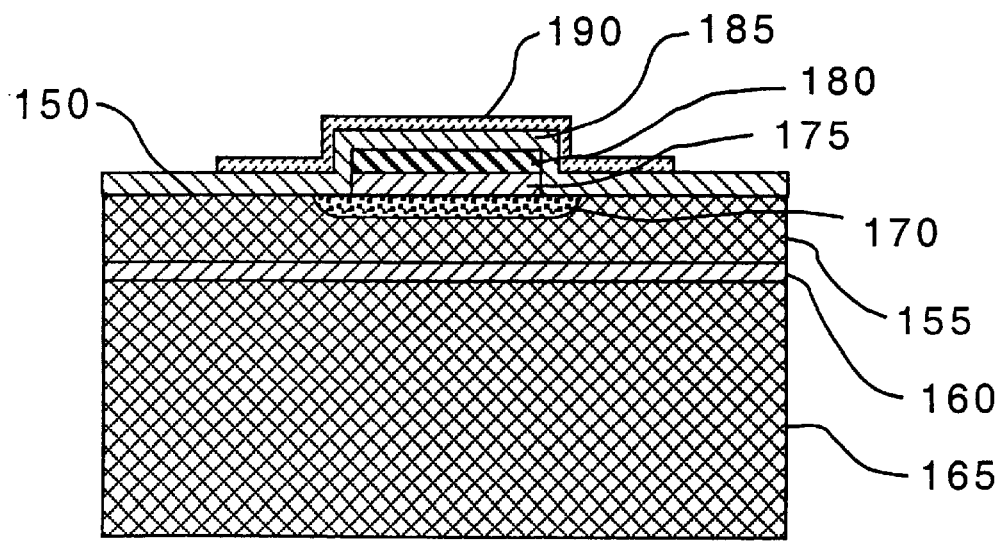
Figure 11D:
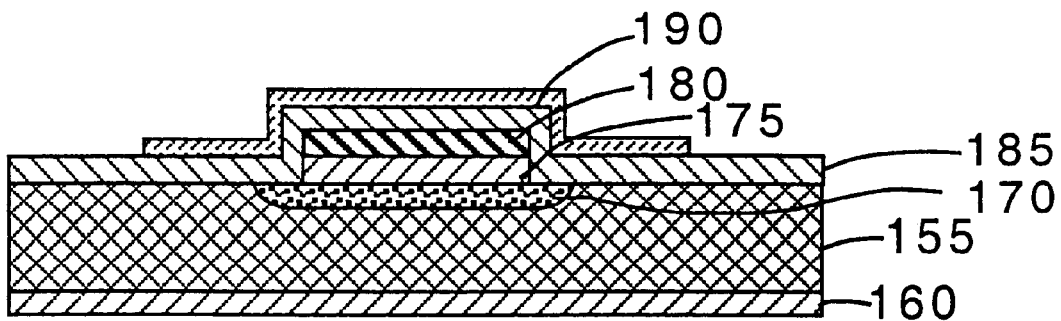
Figure 11E:
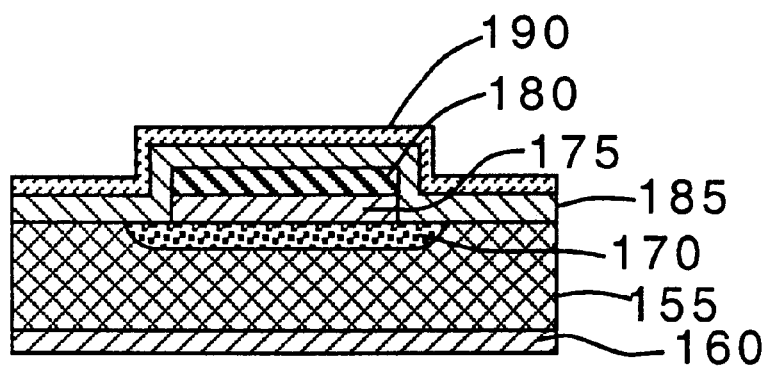

FIGS. 11*a* through 11*e* illustrate a preferred method for manufacturing sensor element 30 that allows for the manufacture of sensor element 30 so that it can be shaped to fit in complex shaped recesses 20, for example those that follow the curvature of a blade used in a surgical tool. As shown in FIG. 11*a,* the process begins with a silicon-on-insulator wafer 150 which is comprised of three layers: a top layer of silicon 155 that will form semiconductor substrate 35, an insulating layer 160 made of, for example, silicon dioxide, and a bottom layer of silicon 165 that provides additional thickness to allow ease of handling during the manufacturing process. FIG. 11*b* shows the silicon-on-insulator wafer 150 after sensor or sensors 40, sensor array 45, electrodes 50, electrical traces 52, electrical contacts 60 and circuitry 55 have been formed according to the known techniques described above. For illustration purposes, a typical transistor structure is shown in FIG. 11*b* where there is a doped region 170, a gate oxide layer 175, a polysilicon gate 180, and a passivation layer 185 made of, for example, silicon nitride. The shaping of the silicon-on-insulator wafer 150 begins, as shown in FIG. 11*c,* with the addition of a layer of photoresist 190 patterned to define the desired outline of semiconductor substrate 35, for example the curvature of blade 10. Preferably, photoresist 190 is patterned to match the shape of recess 20. Photoresist 190 may be applied to silicon-on-insulator wafer 150 using an appropriately patterned mask and any commonly known technique, such as spinning. Then, as shown in FIG. 11*d,* preferably using a deep reactive ion etcher which has a much higher etch rate of silicon versus oxide, the lower layer of silicon 165 is removed. Next, as shown in FIG. 11*e,* a deep reactive ion etcher is used to remove the portions of passivation layer 185, top layer of silicon 155 and insulating layer 160 that are not covered by photoresist 190. Alternatively, as described in W. Kern and C. H. Deckert, "Chemical Etching," in Thin Film Processes, ed. J. L. Vossen and W. Kern, New York, Academic Press, 1978, pp. 401–496, instead of using reactive ion etching, various wet etches may be used to etch these layers. Additionally, as described in H. F. Winters and J. W. Coburn, "The etching of silicon with XeF2 vapor," Applied Physics Letters, vol. 34, no. 1, Jan. 1978, pp. 70–73, xenon difluoride may be used to remove any unwanted silicon. Finally, photoresist 190 is removed using an oxygen plasma or chemical solvent such as acetone, leaving behind what ultimately forms semiconductor substrate 35 having the various elements formed thereon. Insulating layer 160 may be removed, or may be left in place, in which case it would provide additional electrical isolation between sensor element 30 and blade 10. As can be seen, by using the silicon-on-insulator method described above, which delays the removal of the bottom layer of silicon 165 to the terminal steps of the process, a thin semiconductor substrate 35, on the order of 100 micrometers, can be made while still utilizing a much thicker working product during processing. A typical silicon-on-insulator wafer is on the order of 500 micrometers thick.

According to an alternate embodiment, after application of photoresist 190 as shown in FIG. 11*c,* a deep reactive ion etch step that stops on insulating layer 160 may be used. At that point, in a fashion similar to that described in K. S. Lebouitz and A. P. Pisano, "Microneedles and Microlancets Fabricated Using SOI Wafers and Isotropic Etching," Proceedings of the Electrochemical Society, Vol. 98–14, pp. 235–244, 1998, the disclosure of which is incorporated herein by reference, insulating layer 160 may be etched with a chemical, such as hydrofluoric acid, to separate upper silicon layer 155 from lower layer of silicon 165. The process would then continue as shown and described in connection with FIG. 11*e*. This alternate embodiment thus avoids the need to etch away lower layer of silicon 165.

According to a further alternate embodiment, instead of using silicon-on-insulator wafer 150 during the manufacturing process, a standard silicon wafer, typically on the order of 500 micrometers, may be used. In this embodiment, rather than removing the bottom layer of silicon 165, the standard silicon wafer is ground down to a desired thickness after the circuitry and sensors are formed thereon. According to still a further alternate embodiment, a thinned silicon wafer on the order of 250 micrometers or less may be used. In the embodiment, the entire fabrication process can be performed without the need to remove a bottom layer of silicon 165 or to grind the thinned silicon wafer down after processing.

Figures 12, 13:
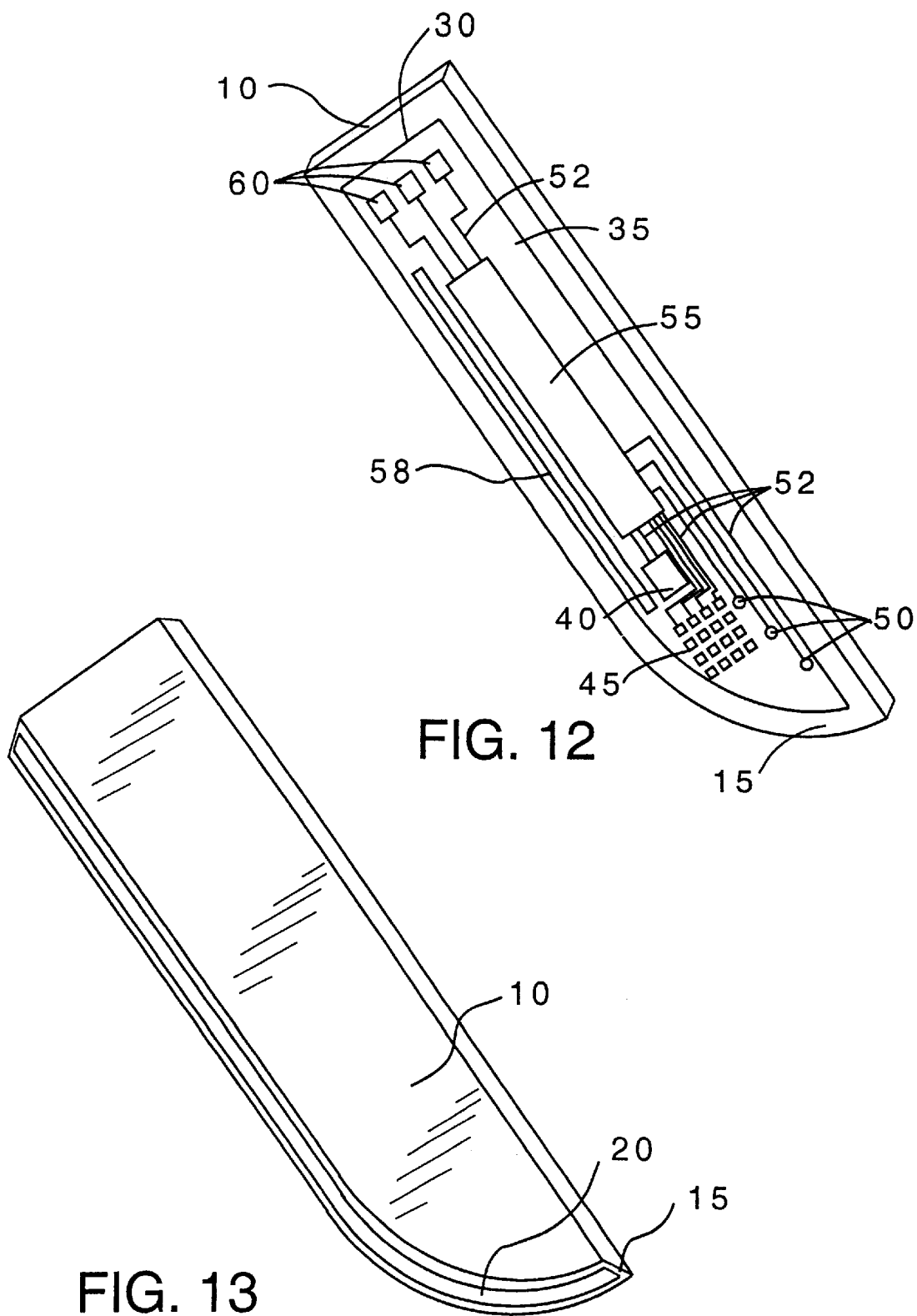
FIG. 12 is an isometric view of an alternate embodiment of a blade having a sensor element mounted therein.
FIG. 13 is an isometric view of a blade according to a further alternate embodiment.

Referring to FIG. 12, an alternate embodiment of the present invention is shown wherein blade 10 comprises what is known in the art as a half blade. A half blade is a blade that has been machined such that the sharp edge is located at the surface on one side of the blade rather than in the midsection of the blade. In other words, rather than beveling both sides of the blade to form an edge that is sharp in the middle, only one side of the blade is beveled to form the sharp edge at the surface of the other side of the blade. Such a configuration allows recess 20, and thus sensor element 30, to be located even closer to the edge 15 of the blade.

According to still a further embodiment of the present invention, recess 20 can be machined in edge 15 of blade 10 which is of the half-blade variety as shown in FIG. 13. The recess 20 can be made to follow the entire curve of blade 10, as is the case in FIG. 13, or simply a portion of the curve of blade 10. Then, sensor element 30 can be shaped so as to fit into recess 20, thus allowing a high sensor area at the cutting edge. Since the top layer of silicon 155 of silicon-on-insulator wafer 150 is thin, on the order of 100 micrometers, and flexible, sensor element 30 can be shaped to fit a curved surface.

Figure 14:
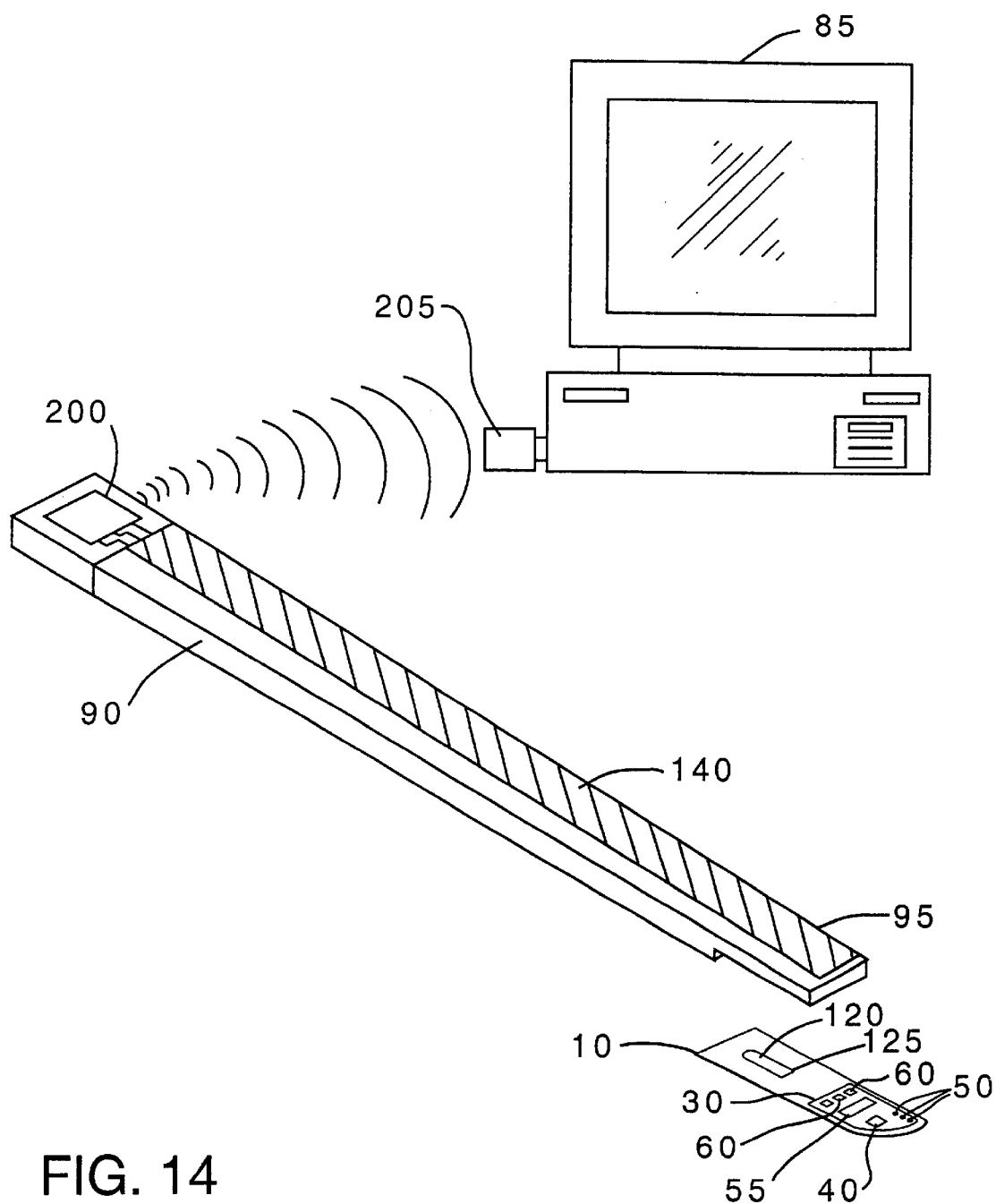
FIG. 14 is an isometric view of a blade affixed to a handle according to an aspect of the present invention wherein the handle is provided with a wireless transmitter that is in communication with a wireless receiver coupled to a computer.

Referring to FIG. 14, handle 90 may be provided with wireless transmitter 200, coupled to ribbon connector 140, that is in communication with wireless receiver 205 of computer 85. Wireless transmitter 200 and wireless receiver 205 may, for example, employ RF or infrared transmission. A suitable example of wireless transmitter 200 is the model TX20B-S1 wireless transmitter sold by Omega Engineering, Inc. located in Stamford, Connecticut, and a suitable example of wireless receiver 205 is the model RX 22 wireless receiver also sold by Omega Engineering, Inc. Power is supplied to the handle and combination shown in FIG. 14 by way of a battery, not shown. The configuration shown in FIG. 14 thus enables data to be transmitted to computer 85 for analysis and display without the need for any physical wires or cables, which tend to restrict the movement of the user. Although wireless transmitter 200 and wireless receiver 205 are shown in FIG. 14 in connection with the embodiment of handle 90 shown in FIGS. 6–10, wireless transmitter 200 and wireless receiver 205 may also be utilized in connection with the embodiment of handle 70 shown in FIG. 4, wherein sensor element 30 would be couple to wireless transmitter 200 through wires 75.

Figure 15:
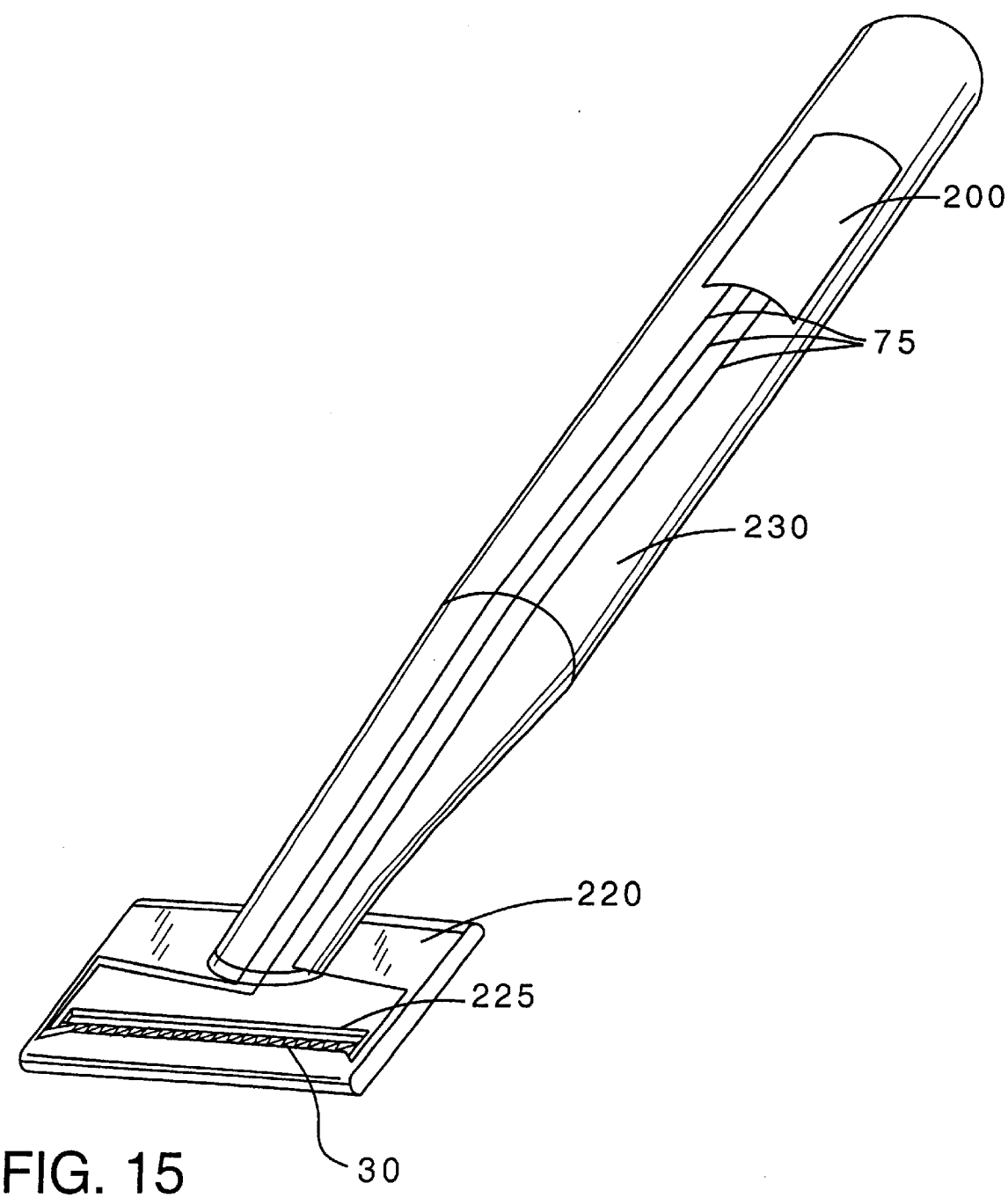
FIG. 15 is an isometric view of an alternate embodiment of the present invention, partially in section, comprising a razor blade having a sensor element mounted therein affixed to a cartridge in turn affixed to a handle.
Figure 16:
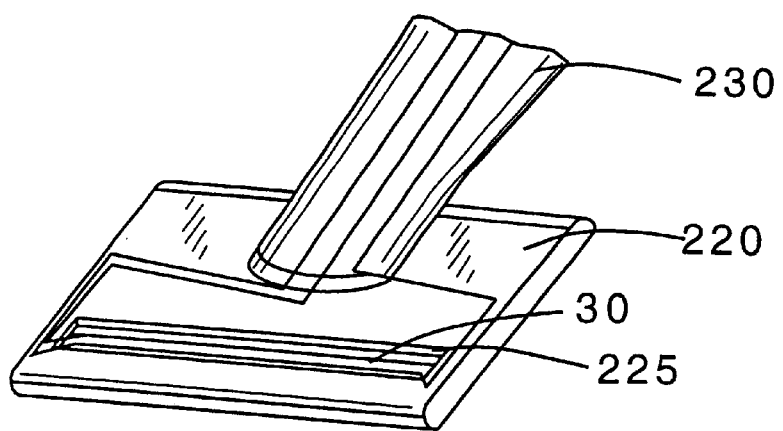
FIG. 16 is a more detailed isometric view, partially in section, of a portion of the razor blade having a sensor element mounted therein affixed to a cartridge in turn affixed to a handle shown in FIG. 15.

Referring to FIGS. 15 and 16, the present invention may be used in connection with a consumer cutting blade such as a razor blade. Shown in FIGS. 15 and 16 is a typical consumer razor blade system including a cartridge 220 having a one or more blades 225 mounted therein, and handle 230 to which cartridge 220 is affixed. At least one of blades 225 includes a recess into which sensor element 30 is affixed. Wires 75, or, alternatively a ribbon connector, connect sensor element 30 to wireless transmitter 200.

Figure 17:
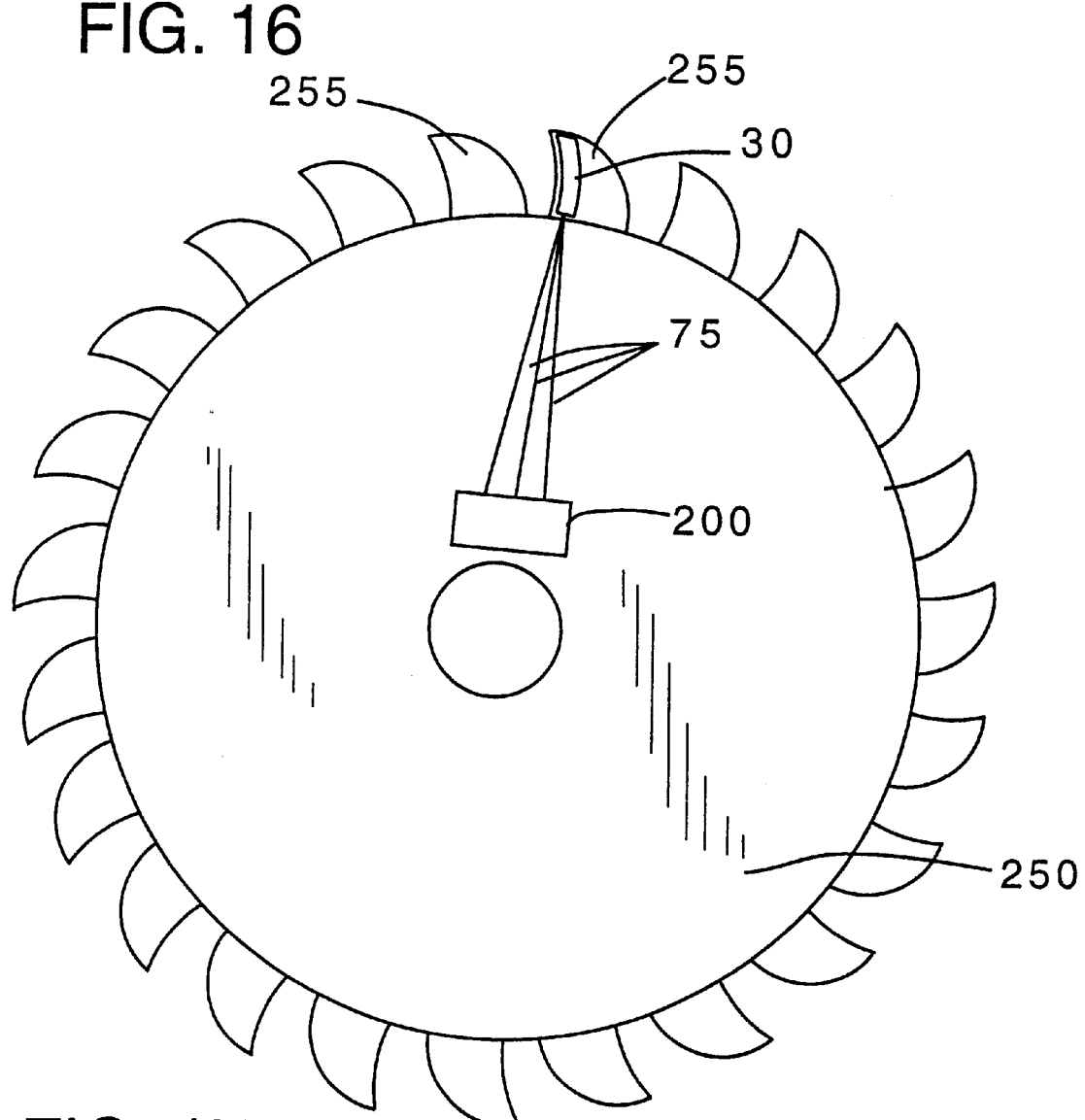
FIG. 17 is a top plan view of a further alternate embodiment of the present invention comprising a saw blade having a sensor element mounted thereon.

The present invention may also be used in connection with various industrial cutting applications. For example, FIG. 17 shows a saw blade 250 having a plurality of cutting teeth 255. At least one of the cutting teeth 255 includes a recess into which sensor element 30 is affixed. Wires 75, or, alternatively a ribbon connector, connect sensor element 30 to wireless transmitter 200.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions. For example, although portions of the description herein have shown the present invention as part of a surgical knife or scalpel, it is to be understood that the invention could form part of other surgical tools, such as the blade of a scissor or microcutter or a part of a suturing device, a trocar or a laparoscopic mechanical cutting tool such as a laparoscopic scissor. It should also be understood that the present invention may be applied not only in traditional surgery, but also to minimally invasive surgery and to robotic surgery. Finally, the term cutting as used herein is intended to cover the act of penetrating or severing with a sharp edge, including, but not limited to, puncturing as with a needle or shearing.

What is claimed is:

1. A cutting instrument, comprising:
    a metal blade having a cutting edge and a recess formed in a first side thereof, and
    a semiconductor substrate affixed to said blade in said recess, said semiconductor substrate having at least one sensor formed thereon to detect at least one characteristic of material adjacent said cutting edge.

2. A cutting instrument according to claim 1, wherein a portion of said recess follows said cutting edge, and said semiconductor substrate is shaped such that when affixed to said blade in said recess, a portion of said semiconductor substrate is mounted adjacent to said cutting edge.

3. A cutting instrument according to claim 2, wherein said semiconductor substrate is shaped to match a shape of said recess.

4. A cutting instrument according to claim 1, wherein said sensor comprises a strain sensor.

5. A cutting instrument according to claim 4, wherein said strain sensor comprises a resistor.

6. A cutting instrument according to claim 1, wherein said sensor comprises a pressure sensor.

7. A cutting instrument according to claim 6, wherein said pressure sensor comprises a strain sensor on top of a diaphragm.

8. A cutting instrument according to claim 1, wherein said sensor comprises a nerve sensor.

9. A cutting instrument according to claim 8, wherein said nerve sensor comprises at least one gold electrode.

10. A cutting instrument according to claim 1, wherein said sensor comprises a temperature sensor.

11. A cutting instrument according to claim 10, wherein said temperature sensor comprises a resistor.

12. A cutting instrument according to claim 1, wherein said sensor comprises a density sensor.

13. A cutting instrument according to claim 12, wherein said density sensor comprises a piezoelectric ultrasonic sensor.

14. A cutting instrument according to claim 1, wherein said sensor senses an aspect of movement of said blade.

15. A cutting instrument according to claim 14, wherein said sensor comprises one or more of an accelerometer and a gyroscope.

16. A cutting instrument according to claim 1, wherein said at least one sensor comprises an array of sensors.

17. A cutting instrument according to claim 1, further comprising a handle, said blade having said semiconductor substrate affixed thereto being affixed to said handle.

18. A cutting instrument according to claim 17, said blade having said semiconductor substrate affixed thereto being electrically coupled to said handle.

19. A cutting instrument according to claim 18, said semiconductor substrate and said handle each having at least one electrical contact, said at least one electrical contact of said semiconductor substrate being coupled to said at least one electrical contact of said handle when said blade is affixed to said handle.

20. A cutting instrument according to claim 19, further comprising means for providing a seal between said handle and said blade, said seal surrounding said electrical contacts.

21. A cutting instrument according to claim 19, wherein said handle includes an electrical connector and said at least one electrical contact of said handle is coupled to said electrical connector.

22. A cutting instrument according to claim 19, wherein said handle includes a wireless transmitter and said at least one electrical contact of said handle is coupled to said wireless transmitter.

23. A cutting instrument according to claim 18, wherein said handle includes an electrical connector.

24. A cutting instrument according to claim 18, wherein said handle includes a wireless transmitter.

25. A cutting instrument according to claim 24, further comprising a computer having a wireless receiver in communication with said wireless transmitter, said computer being adapted to display information to a user based on signals generated by said at least one sensor.

26. A cutting instrument according to claim 24, further comprising a computer having a wireless receiver in communication with said wireless transmitter, said computer being adapted to store data based on signals generated by said at least one sensor.

27. A cutting instrument according to claim 18, further comprising a computer, said handle being coupled to said computer.

28. A cutting instrument according to claim 27, said computer being adapted to display information to a user based on signals generated by said at least one sensor.

29. A cutting instrument according to claim 27, said computer being adapted to store data based on signals generated by said at least one sensor.

30. A cutting instrument according to claim 1, further comprising a handle and means for connecting and electrically coupling said blade having said semiconductor substrate affixed thereto to said handle.

31. A cutting instrument according to claim 30, wherein said handle includes an electrical connector.

32. A cutting instrument according to claim 30, wherein said handle includes a wireless transmitter.

33. A cutting instrument according to claim 1, wherein said blade comprises a half-blade.

34. A cutting instrument according to claim 1, wherein said recess is formed in said cutting edge.

35. A cutting instrument according to claim 1, said semiconductor substrate having circuitry formed thereon coupled to said at least one sensor, said circuitry comprising one or more amplifiers.

36. A cutting instrument according to claim 35, said at least one sensor comprising a plurality of sensors, said circuitry further comprising logic circuitry for multiplexing signals produced by said plurality of sensors.

37. A cutting instrument according to claim 36, said semiconductor substrate having one or more electrical contacts formed thereon, said circuitry being coupled to said one or more electrical contacts.

38. A cutting instrument according to claim 35, said semiconductor substrate having one or more electrical contacts formed thereon, said circuitry being coupled to said one or more electrical contacts.

39. A cutting instrument according to claim 1, said semiconductor substrate further comprising means for delivering a fluid.

40. A cutting instrument, comprising:
  a metal blade having a cutting edge and a recess formed in a first side thereof; and
  a semiconductor substrate affixed to said blade in said recess, said semiconductor substrate having means for sensing at least one of strain, pressure, the presence of a nerve, density, temperature and movement in relation to a material adjacent said cutting edge.

41. A cutting instrument according to claim 40, further comprising means for electrically coupling said semiconductor substrate to a computer, said computer being adapted to do at least one of display information to a user based on signals generated by said sensing means and store data based on signals generated by said sensing means.

42. A cutting instrument according to claim 40, wherein a portion of said recess follows said cutting edge, and said semiconductor substrate is shaped such that when affixed to said blade in said recess, a portion of said semiconductor substrate is mounted adjacent to said cutting edge.

43. A cutting instrument according to claim 42, wherein said semiconductor substrate is shaped to match a shape of said recess.

44. A cutting instrument according to claim 40, further comprising a handle and means for connecting and electrically coupling said blade having said semiconductor substrate affixed thereto to said handle.

45. A cutting instrument according to claim 44, further comprising means for electrically coupling said handle to a computer, said computer being adapted to do at least one of display information to a user based on signals generated by said sensing means and store data based on signals generated by said sensing means.

46. A cutting instrument according to claim 44, wherein said handle includes an electrical connector.

47. A cutting instrument according to claim 44, wherein said handle includes a wireless transmitter.

48. A cutting instrument according to claim 40, further comprising a handle, said blade having said semiconductor substrate affixed thereto being connected and electrically coupled to said handle.

49. A cutting instrument according to claim 48, further comprising means for electrically coupling said handle to a computer, said computer being adapted to do at least one of display information to a user based on signals generated by said sensing means and store data based on signals generated by said sensing means.

50. A cutting instrument according to claim 48, wherein said handle includes an electrical connector.

51. A cutting instrument according to claim 48, wherein said handle includes a wireless transmitter.

52. A cutting instrument according to claim 40, wherein said blade comprises a half-blade.

53. A cutting instrument according to claim 40, wherein said recess is formed in said cutting edge.

54. A cutting instrument according to claim 40, said semiconductor substrate having means for amplifying signals produced by said sensing means.

55. A cutting instrument according to claim 40, said semiconductor substrate having means for multiplexing signals produced by said sensing means.

56. A cutting instrument according to claim 40, said semiconductor substrate further comprising means for delivering a fluid.

* * * * *